United States Patent
Gilbert

(10) Patent No.: US 7,956,620 B2
(45) Date of Patent: Jun. 7, 2011

(54) SYSTEM AND METHOD FOR AUGMENTED IMPEDANCE SENSING

(75) Inventor: James A. Gilbert, Boulder, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 100 days.

(21) Appl. No.: 12/540,190

(22) Filed: Aug. 12, 2009

(65) Prior Publication Data

US 2011/0037484 A1   Feb. 17, 2011

(51) Int. Cl.
   *G01R 27/28*   (2006.01)
   *A61B 18/04*   (2006.01)
(52) U.S. Cl. .......................................... 324/649; 606/34
(58) Field of Classification Search .................. None
   See application file for complete search history.

(56) References Cited

U.S. PATENT DOCUMENTS

| | | | |
|---|---|---|---|
| 3,495,584 A | 2/1970 | Schwalm |
| 3,515,943 A | 6/1970 | Warrington |
| 3,595,221 A | 7/1971 | Blackett |
| 3,611,053 A | 10/1971 | Rowell |
| 3,697,808 A | 10/1972 | Lee |
| 3,801,800 A | 4/1974 | Newton |
| 4,188,927 A | 2/1980 | Harris |
| 4,200,104 A | 4/1980 | Harris |
| 4,231,372 A | 11/1980 | Newton |
| 4,416,276 A | 11/1983 | Newton et al. |
| 4,416,277 A | 11/1983 | Newton et al. |
| 4,569,345 A | 2/1986 | Manes |
| 4,739,759 A | 4/1988 | Rexroth et al. |
| 4,767,999 A | 8/1988 | VerPlanck |
| 4,848,335 A | 7/1989 | Manes |
| 4,860,745 A | 8/1989 | Farin et al. |
| 4,887,199 A | 12/1989 | Whittle |
| 5,300,068 A | 4/1994 | Rosar et al. |
| 5,400,267 A | 3/1995 | Denen et al. |
| 5,445,635 A | 8/1995 | Denen |
| 5,531,774 A | 7/1996 | Schulman et al. |
| 5,749,871 A | 5/1998 | Hood et al. |
| 5,817,093 A | 10/1998 | Williamson et al. |
| 5,830,212 A | 11/1998 | Cartmell |

(Continued)

FOREIGN PATENT DOCUMENTS

DE    179607    3/1905

(Continued)

OTHER PUBLICATIONS

U.S. Appl. No. 12/057,557, filed Mar. 28, 2008.

(Continued)

*Primary Examiner* — Roberto Velez

(57) ABSTRACT

An impedance monitoring circuit for an electrosurgical generator is disclosed. The monitoring circuit includes an isolation transformer coupled to at least one of an active terminal and a return terminal of an electrosurgical generator, wherein the isolation transformer includes a primary winding coupled to a reference resistor and a secondary winding coupled to a load. The monitoring circuit also includes a driver configured to transmit a sensor signal to the reference resistor and the load, a primary converter coupled to the reference resistor and the load and configured to detect a primary converted signal as a function of the sensor signal passing through the reference resistor and the load. The monitoring circuit further includes a secondary converter coupled to the driver and configured to detect a secondary converted signal as a function of the sensor signal prior to passing through the reference resistor and the load and a controller configured to determine a fault condition based on the primary and secondary converted signals.

18 Claims, 7 Drawing Sheets

U.S. PATENT DOCUMENTS

| | | | |
|---|---|---|---|
| 5,871,481 A | 2/1999 | Kannenberg et al. | |
| 5,971,980 A | 10/1999 | Sherman | |
| 5,971,981 A | 10/1999 | Hill et al. | |
| 6,142,992 A | 11/2000 | Cheng et al. | |
| 6,228,081 B1 | 5/2001 | Goble | |
| 6,231,569 B1 | 5/2001 | Bek | |
| 6,235,020 B1 | 5/2001 | Cheng et al. | |
| 6,273,886 B1 | 8/2001 | Edwards | |
| 6,296,636 B1 | 10/2001 | Cheng et al. | |
| 6,358,245 B1 | 3/2002 | Edwards | |
| 6,398,779 B1 | 6/2002 | Buysse et al. | |
| 6,402,742 B1 | 6/2002 | Blewett et al. | |
| 6,508,815 B1 | 1/2003 | Strul | |
| 6,547,786 B1 | 4/2003 | Goble | |
| 6,565,562 B1 | 5/2003 | Shah et al. | |
| 6,645,198 B1 | 11/2003 | Bommannan et al. | |
| 6,652,514 B2 | 11/2003 | Ellman | |
| 6,682,527 B2 | 1/2004 | Strul | |
| 6,693,782 B1 | 2/2004 | Lash | |
| 6,740,079 B1 | 5/2004 | Eggers | |
| 6,783,523 B2 | 8/2004 | Qin | |
| 6,923,804 B2 | 8/2005 | Eggers et al. | |
| 6,936,047 B2 | 8/2005 | Nasab et al. | |
| 6,994,707 B2 | 2/2006 | Ellman et al. | |
| 7,004,174 B2 | 2/2006 | Eggers et al. | |
| 7,041,096 B2 | 5/2006 | Malis et al. | |
| 7,074,217 B2 | 7/2006 | Strul et al. | |
| RE39,358 E | 10/2006 | Goble | |
| 7,122,031 B2 | 10/2006 | Edwards et al. | |
| 7,195,627 B2 | 3/2007 | Amoah et al. | |
| 7,211,081 B2 | 5/2007 | Goble | |
| 7,226,447 B2 | 6/2007 | Uchida et al. | |
| 7,258,688 B1 | 8/2007 | Shah et al. | |
| 7,407,502 B2 | 8/2008 | Strul et al. | |
| 7,465,302 B2 | 12/2008 | Odell et al. | |
| 7,479,140 B2 | 1/2009 | Ellman et al. | |
| 2002/0165530 A1 | 11/2002 | Harano et al. | |
| 2005/0004570 A1 | 1/2005 | Chapman et al. | |
| 2005/0101951 A1 | 5/2005 | Wham et al. | |
| 2006/0161148 A1 | 7/2006 | Behnke | |
| 2008/0082094 A1 | 4/2008 | McPherson et al. | |
| 2009/0157071 A1 | 6/2009 | Wham et al. | |
| 2009/0157072 A1 | 6/2009 | Wham et al. | |
| 2009/0157075 A1 | 6/2009 | Wham et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 608609 | 8/1994 |
| EP | 0617925 | 10/1994 |
| EP | 836868 | 4/1998 |
| EP | 1051948 | 11/2000 |
| EP | 1053720 | 11/2000 |
| EP | 1293171 | 3/2003 |
| EP | 1 472 984 | 11/2004 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| SU | 166452 | 1/1965 |
| SU | 727201 | 4/1980 |
| WO | WO 96/39086 | 12/1996 |
| WO | WO96/39086 | 12/1996 |

OTHER PUBLICATIONS

U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedence" Am. J. MI, Jan. Mar. 1964, pp. 16-27.

Cosman et al., "Methods of Making Nervous System Lesions" in William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Cosman et al., "Radiofrequency Lesion Generation and Its Effect on Tissue Impedance" Applied Neurophysiology 51: (1988) pp. 230-242.

Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report EP10172636 dated Dec. 6, 2010.
European Search Report for EP 10 18 0964 dated Dec. 22, 2010.

SYSTEM AND METHOD FOR AUGMENTED IMPEDANCE SENSING

BACKGROUND

1. Technical Field

The present disclosure relates to electrosurgical apparatuses, systems and methods. More particularly, the present disclosure is directed to electrosurgical systems configured to monitor impedance.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue.

In bipolar electrosurgery, one of the electrodes of the handheld instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

Bipolar electrosurgical techniques and instruments can be used to coagulate blood vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. In order to achieve one of these desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

In monopolar electrosurgery, the active electrode is typically a part of the surgical instrument held by the surgeon that is applied to the tissue to be treated. A patient return electrode is placed remotely from the active electrode to carry the current back to the generator and safely disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

The first types of return electrodes were in the form of large metal plates covered with conductive gel. Later, adhesive electrodes were developed with a single metal foil covered with conductive gel or conductive adhesive. However, one problem with these adhesive electrodes was that if a portion peeled from the patient, the contact area of the electrode with the patient decreased, thereby increasing the current density at the adhered portion and, in turn, increasing the heating at the tissue contact site. This risked burning the patient in the area under the adhered portion of the return electrode if the tissue was heated beyond the point where circulation of blood could cool the skin.

To address this problem various return electrodes and hardware circuits, generically called Return Electrode Contact Quality Monitors (RECQMs), were developed. Such systems relied on measuring impedance at the return electrode to calculate a variety of tissue and/or electrode properties. These systems detected peeling by identifying changes in impedance of the return electrodes. In bipolar and monopolar systems it is desirable to monitor impedance to ensure proper operation of the electrosurgical generator and associated instruments and return electrodes.

SUMMARY

According to one embodiment of the present disclosure, an impedance monitoring circuit for an electrosurgical generator is disclosed. The monitoring circuit includes an isolation transformer coupled to at least one of an active terminal and a return terminal of an electrosurgical generator, wherein the isolation transformer includes a primary winding coupled to a reference resistor and a secondary winding coupled to a load. The monitoring circuit also includes a driver configured to transmit a sensor signal to the reference resistor and the load, a primary converter coupled to the reference resistor and the load and configured to detect a primary converted signal as a function of the sensor signal passing through the reference resistor and the load. The monitoring circuit further includes a secondary converter coupled to the driver and configured to detect a secondary converted signal as a function of the sensor signal prior to passing through the reference resistor and the load and a controller including a preprogrammed offset value. The controller is configured to determine a fault condition based on the primary and secondary converted signals and the offset value.

According to another aspect of the present disclosure, an impedance monitoring circuit for an electrosurgical generator is disclosed. The monitoring circuit includes an isolation transformer coupled to at least one of an active terminal and a return terminal of an electrosurgical generator, wherein the isolation transformer includes a primary winding coupled to a reference resistor and a secondary winding coupled to a load. The monitoring circuit also includes a driver configured to transmit a sensor signal to the reference resistor and the load, a primary converter coupled to the reference resistor and the load and configured to detect a primary converted signal as a function of the sensor signal passing through the reference resistor and the load. The monitoring circuit further includes a secondary converter coupled to the driver and configured to detect a secondary converted signal as a function of the sensor signal prior to passing through the reference resistor and the load and a controller configured to determine a fault condition based on the primary and secondary converted signals.

A method for detecting a fault in an impedance monitoring circuit is also contemplated by the present disclosure. The method includes the steps of: transmitting a sensor signal to a reference resistor coupled to a primary winding of an isolation transformer and a load coupled to a secondary winding of the isolation transformer and detecting a primary converted signal as a function of the sensor signal passing through the reference resistor and the load. The method also includes the steps of detecting a secondary converted signal as a function of the sensor signal prior to passing through the reference resistor and the load and determining a fault condition based on the primary and secondary converted signals.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1:
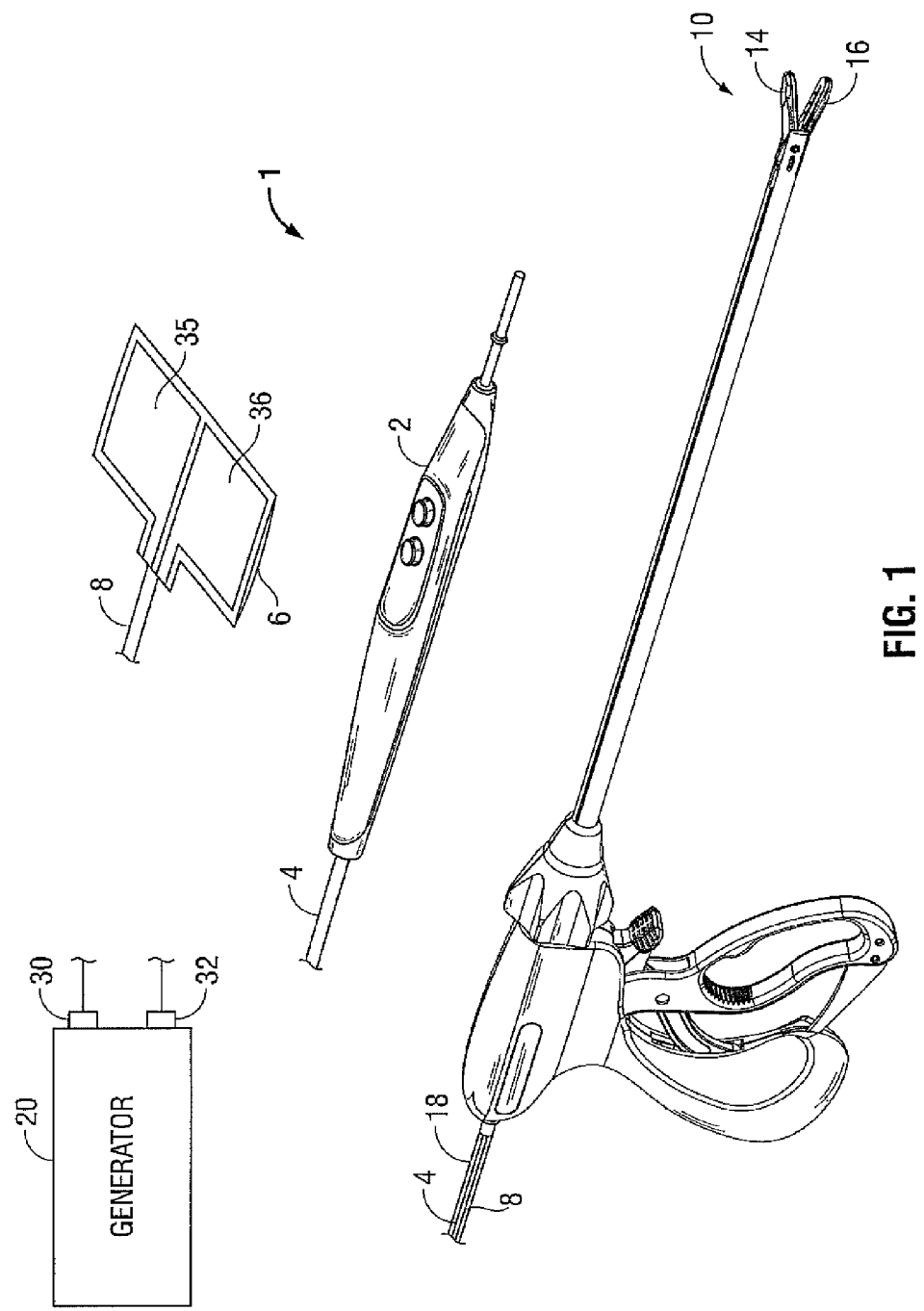
FIG. 1 is a schematic block diagram of an electrosurgical system according to one embodiment of the present disclosure.

FIG. 1 is a schematic illustration of a bipolar and monopolar electrosurgical system 1 according to one embodiment of the present disclosure. The system 1 includes a monopolar electrosurgical instrument 2 having one or more electrodes for treating tissue of a patient (e.g., electrosurgical cutting probe, ablation electrode(s), etc.). Electrosurgical RF energy is supplied to the instrument 2 by a generator 20 via a supply line 4, which is connected to an active terminal 30 (FIG. 2) of the generator 20, allowing the instrument 2 to coagulate, seal, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8 respectively.

The system 1 may include a plurality of return electrodes 6 that are arranged to minimize the chances of tissue damage by maximizing the overall contact area with the patient. In addition, the generator 20 and the return electrode 6 may be configured for monitoring so-called "tissue-to-patient" contact to insure that sufficient contact exists therebetween to further minimize chances of tissue damage.

The system 1 also includes a bipolar electrosurgical forceps 10 having one or more electrodes for treating tissue of a patient. The electrosurgical forceps 10 include opposing jaw members having an active electrode 14 and a return electrode 16 disposed therein. The active electrode 14 and the return electrode 16 are connected to the generator 20 through cable 18, which includes the supply and return lines 4, 8 coupled to the active and return terminals 30, 32, respectively. The electrosurgical forceps 10 are coupled to the generator 20 at a connector having connections to the active and return terminals 30 and 32 (e.g., pins) via a plug (not explicitly shown) disposed at the end of the cable 18, wherein the plug includes contacts from the supply and return lines 4, 8.

The generator 20 may be any suitable type (e.g., electrosurgical, microwave, etc.) and may include a plurality of connectors to accommodate various types of electrosurgical instruments (e.g., instrument 2, electrosurgical forceps 10, etc.). Further, the generator 20 may be configured to operate in a variety of modes such as ablation, monopolar and bipolar cutting coagulation, etc. It is envisioned that the generator 20 may include a switching mechanism (e.g., relays) to switch the supply of RF energy between the connectors, such that, for instance, when the instrument 2 is connected to the generator 20, only the monopolar plug receives RF energy. The active and return terminals 30 and 32 may be coupled to a plurality of connectors (e.g., inputs and outputs) of the generator 20 to power a variety of instruments.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 2A:
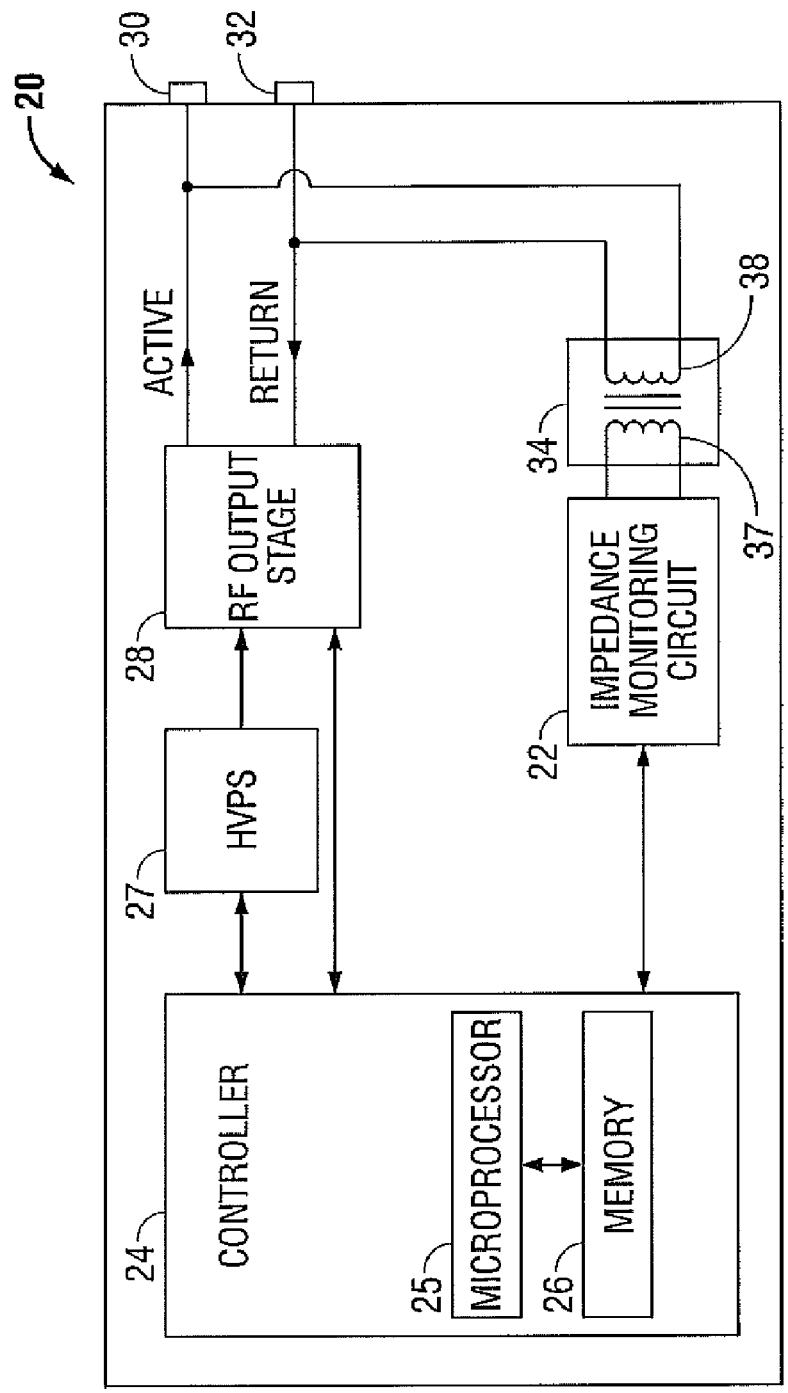
FIG. 2A is a schematic block diagram of a bipolar generator according to an embodiment of the present disclosure.
Figure 2B:
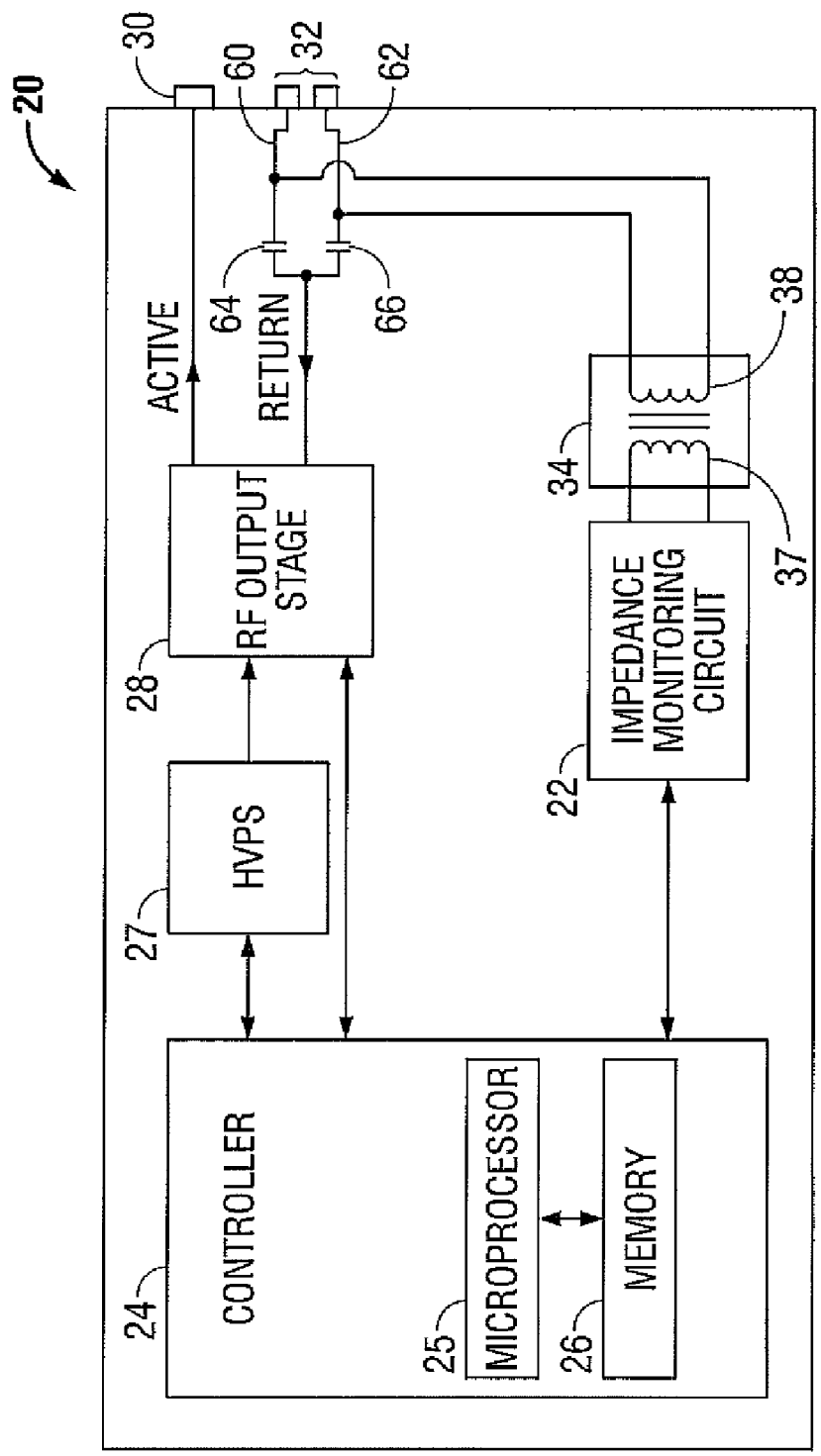
FIG. 2B is a schematic block diagram of a monopolar generator according to an embodiment of the present disclosure.

FIGS. 2A and 2B show a schematic block diagram of the generator 20. FIG. 2A shows the generator 20 in a bipolar configuration and FIG. 2B shows the generator in a monopolar configuration. The generator 20 includes a controller 24, a high voltage DC power supply 27 ("HVPS") and an RE output stage 28. The HVPS 27 is connected to a conventional AC source (e.g., electrical wall outlet) and provides high voltage DC power to an RF output stage 28, which then converts high voltage DC power into RE energy and delivers the RF energy to the active terminal 30. The energy is returned thereto via the return terminal 32.

In particular, the RF output stage 28 generates sinusoidal waveforms of high RE energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop, in which a plurality of sensors measure a variety of tissue and energy properties (e.g., tissue impedance, tissue temperature, output current and/or voltage, etc.), and provide feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

The generator 20 includes an impedance monitoring circuit 22 which is coupled to an isolation transformer 34 that is, in turn, coupled to the active and return terminals 30 and 32, the isolation transformer 34 includes a primary winding 37 coupled to the monitoring circuit 22 and a secondary winding 38 coupled to the active and return terminals 30 and 32. The monitoring circuit 22 detects the impedance of the load (e.g., tissue in contact with instrument 2 or the forceps 10) and transmits the impedance measurements to the controller 24 for determination of treatment completion and other status updates. In addition, the monitoring circuit 22 also detects any faults at the load or within the generator 20 in either bipolar and monopolar configurations. In bipolar configuration as shown in FIG. 2A, the monitoring circuit 22 is coupled to the active and return terminals 30 and 32 and detects the impedance between the active electrode 14 and the return electrode 16 of the forceps 10 and determines whether the electrodes 14 and 16 are shorted and/or the circuit therebetween is open (e.g., no tissue is being grasped).

In monopolar configuration shown in FIG. 2B, the monitoring circuit 22 detects the impedance at the return electrode 6 to determine the adherence of the return electrode 6 to the tissue. More specifically, the return electrode 6 includes a pair of split electrode pads, a first electrode pad 35 and a second electrode pad 36 disposed within the return electrode pad 6 (FIG. 1). The return electrode 6 is in contact with the tissue and returns the electrosurgical energy to the generator 20 via the first and second electrode pads 35 and 36. The return terminal 32 includes a plurality of connections (e.g., leads 60 and 62) corresponding to the number of electrode pads of the return electrode 6. Each of the leads 60 and 62 includes capacitors 64 and 66, respectively and are coupled to the RF output stage 28 to return electrosurgical energy thereto. The leads 60 and 62 are also coupled to the secondary winding 38 of the transformer 34. In one embodiment the return electrode 6 may include a plurality of split electrode pads arranged in pairs that are coupled to a corresponding number of connections.

The controller 24 provides a drive signal, REM CLK, at a specific interrogation frequency to the monitoring circuit 22. REM CLK, is a clock signal generated by the controller 24 at the specific frequency, which may be either a square wave, a sine wave, an impulse or step signal. REM CLK may be a constant, physiologically benign waveform (e.g., 140 kHz, 2 mA) that the monitoring circuit 22 applies to the first electrode pad 35. The drive signal thereafter passes through the patient and is returned to the monitoring circuit 22 via the second electrode pad 36. The monitoring circuit 22 then measures a response signal to the drive signal and monitors the changes in the response signal to determine degree of adhesion of the return electrode pad 6. The response signal (e.g., returning drive signal) is modified by the impedance of the first and second electrode pads 35 and 36. More specifically, as the impedance between the split electrode pads 35 and 36 changes due to peeling of the return electrode pad 6 from the patient, the monitoring circuit 22 then supplies the impedance measurement to the controller 24, which determines whether the impedance is within a desired range. If the impedance is outside the desired range an excessive peeling condition exists with the return electrode pad 6 and the controller 24 issues an alarm and/or adjusts the output of the generator 20 (e.g., terminates RF energy supply). In addition to monitoring the adherence of the return electrode 6 based on the impedance, the monitoring circuit 22 also determines whether the first and second electrode pads 35 and 36 are shorted (e.g., insulation therebetween at the return electrode 6 deteriorated) or open (e.g., the return electrode 6 peeled off the tissue).

Figure 3:
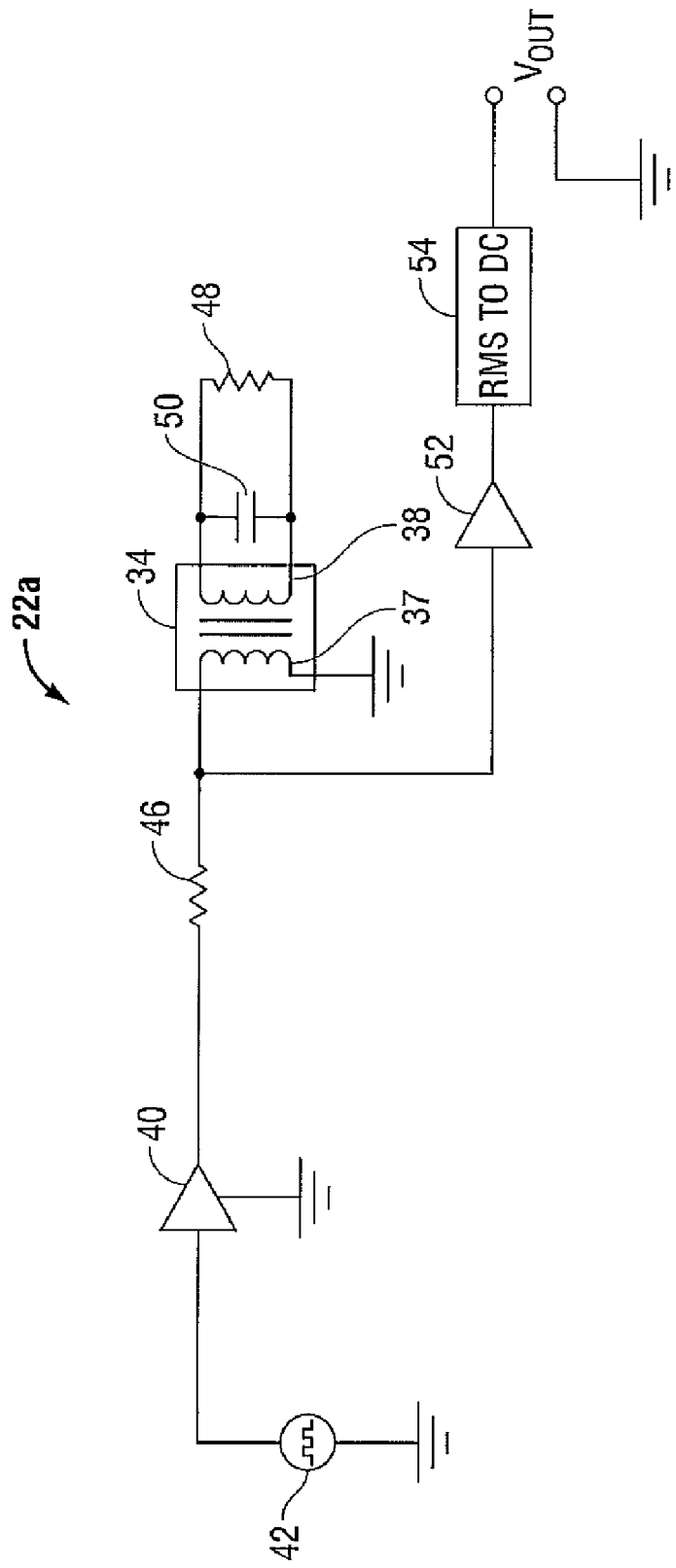
FIG. 3 is a schematic circuit diagram of a detection circuit according to one embodiment of the present disclosure.

FIG. 3, illustrates a monitoring circuit 22a according to one embodiment of the present disclosure. The monitoring circuit 22a includes a driver 40, which may be a level shifter driver, coupled to a clock oscillator 42. The oscillator 42 outputs an oscillator signal, which is a square wave, to the driver 40. In one embodiment, the oscillator signal may have an amplitude from about 0 V to about 5 V. The driver 40 level shifts the oscillator signal from the oscillator 42 to output a sensor signal, which is a square wave having a higher amplitude than the oscillator signal. In one embodiment, the sensor signal may have an amplitude from about 0 V to about 10 V.

The monitoring circuit 22a also includes a reference resistor 46 coupled to the driver 40. The driver circuit 22a is coupled via the transformer 34 to a load 48. The load 48 may be tissue grasped by the forceps 10 or may be the return electrode 6, based on the mode of operation of the generator 20. At the secondary winding 38, the monitoring circuit 22a also includes a band pass filter 50 for filtering out only the sensor signal (e.g., at about 80 kHz).

The monitoring circuit 22a also includes a buffer 52 coupled between the resistor 46 and the transformer 34. The buffer 52 detects the voltage passing through resistor 46 and transmits the detected signal to a primary converter 54 (e.g., RMS to DC) which then transmits the primary converted DC signal as $V_{out}$ to the controller 24 for further processing.

The resistor 46 has a predetermined resistance, $Z_{out}$, which may be from about 1 kΩ to about 10 kΩ. The relatively large resistance of the resistor 46, allows the monitoring circuit 22a to act as a current source, with the resistance converting the sensor signal into current. The resistance, $Z_{out}$, is selected to be larger than a resistance of the load 48, $Z_{load}$, under normal operating conditions. When $Z_{out}$ is larger than $Z_{load}$, $V_{out}$ is approximately proportional to $Z_{load}$. This allows the controller 24 to determine the resistance of the load based on the $V_{out}$. Thus, when $Z_{load}$ is approximately 0, such as when the output is shorted, the controller 24 makes the determination that there exists a short based on the voltage being 0 V. When $Z_{load}$ is much larger than $Z_{out}$, then an open circuit is detected (e.g., when $V_{out}$ is approximately 10V). More specifically, the controller 24 makes the determination of an open circuit based on the amplitude of $V_{out}$, which is proportional to the impedance being larger than $Z_{out}$.

Figure 4:
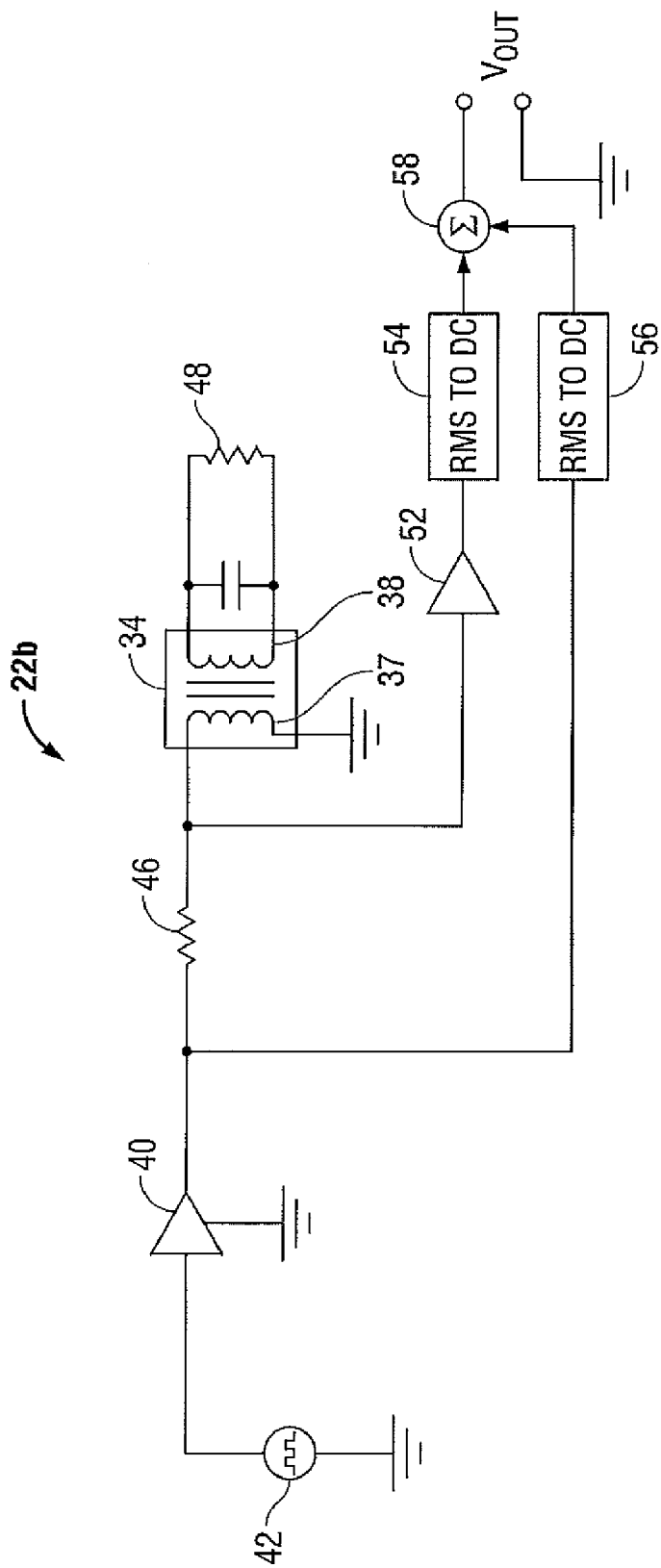
FIG. 4 is a schematic circuit diagram of a detection circuit according to another embodiment of the present disclosure.

FIG. 4 illustrates another embodiment of a monitoring circuit 22b. In addition to the components of the monitoring circuit 22a shown in FIG. 3, and discussed above, the monitoring circuit 22b of includes a secondary converter 56 coupled between the driver 40 and the resistor 46. As discussed above with reference to FIG. 3, the monitoring circuit 22a is configured to determine when the circuit is shorted or open. However, the monitoring circuit 22a may not pinpoint whether the fault condition exists due to the open or shorted circuit or whether one of the components of the monitoring circuit 22a is at fault, which case $V_{out}$ would still be 0. In other words, the monitoring circuit 22a may not determine whether the fault condition exists within the signal chain between the oscillator 42 and the transformer 34.

The secondary converter 56 samples the sensor signal square wave as the signal traverses to the resistor 46. The converter 56 converts the signal to a DC signal and transmits it to a summer 58. Since the converter 56 is disposed between the oscillator 42 and the resistor 46, the converted DC signal corresponds to the unmodified sensor signal being output by the oscillator. As a result, the converter 56 outputs a constant DC offset. The summer 58 is coupled to the primary and secondary converters 54 and 56 and sums the primary and secondary converted signals, thereby adding a constant DC offset proportional to the oscillator signal level and supplying a parsed signal with the DC offset as $V_{out}$ to the controller 24.

In one embodiment, the controller 24 includes a preprogrammed value for the DC offset that the controller 24 subtracts from the $V_{out}$ signal to arrive at the original primary converted signal. The controller 24 then makes a determination of the impedance based on the $V_{out}$ signal minus the DC offset. The controller 24 determines if the parsed signal is associated with a faulty oscillator 42 and/or the driver 40, if the $V_{out}$ is approximately 0 V and thereby does not include the DC offset. The controller 24 determines if the parsed signal is associated with an open circuit, such as when the amplitude of the primary converted signal is nearly unchanged at 10 V. The controller 24 determines whether $V_{out}$ is associated with $Z_{out}$ being much larger than $Z_{load}$—a condition reflective of a shorted circuit and the amplitude of $V_{out}$ signal approaches the DC offset (e.g., when the amplitude of the primary converted signal is approximately 0 V).

Figure 5:
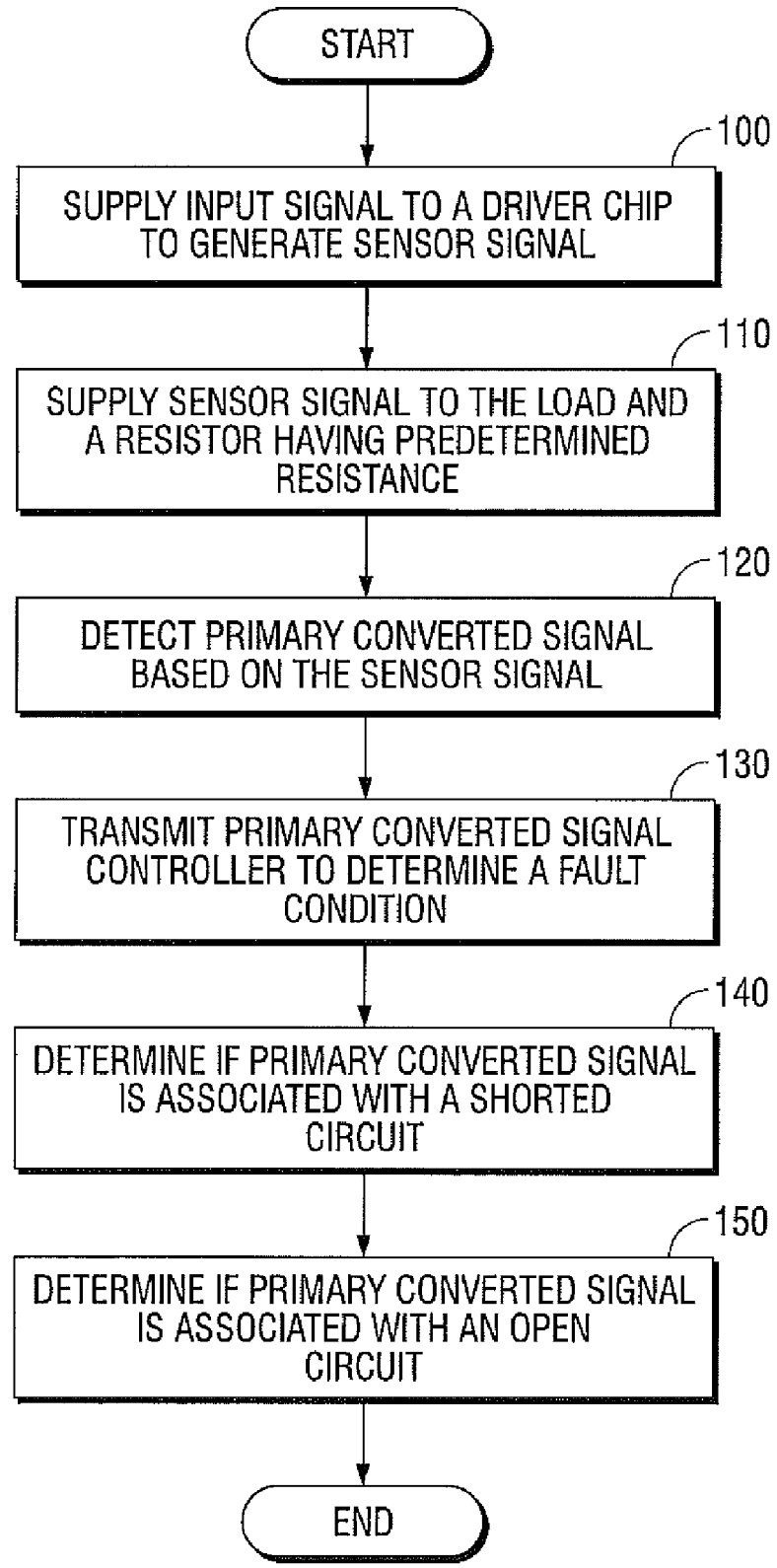
FIG. 5 is a flow chart illustrating a method according to one embodiment of the present disclosure.

FIG. 5 illustrates a method for determining a fault condition based on the $V_{out}$ signal supplied by the monitoring circuit 22a. In step 100, the oscillator 42 supplies an input signal to the driver 40, which generates a sensor signal. In step 110, the sensor signal is supplied to the resistor 46 having a predetermined resistance, $Z_{out}$ and to the load 48 through the isolation transformer. In step 120, primary converted signal is detected based on the sensor signal. In step 130, the converter 54 transmits the primary converted signal to the controller 24 which determines if there is a fault detected by or associated with the monitoring circuit 22b. In step 140, the controller 24 determines if the primary converted signal associated with a shorted circuit, such as when the amplitude (e.g., voltage) of $V_{out}$ is approximately 0. In step 150, the controller 24 determines whether $V_{out}$ is associated with $Z_{load}$ being much larger than $Z_{out}$—a condition reflective of an open circuit.

Figure 6:
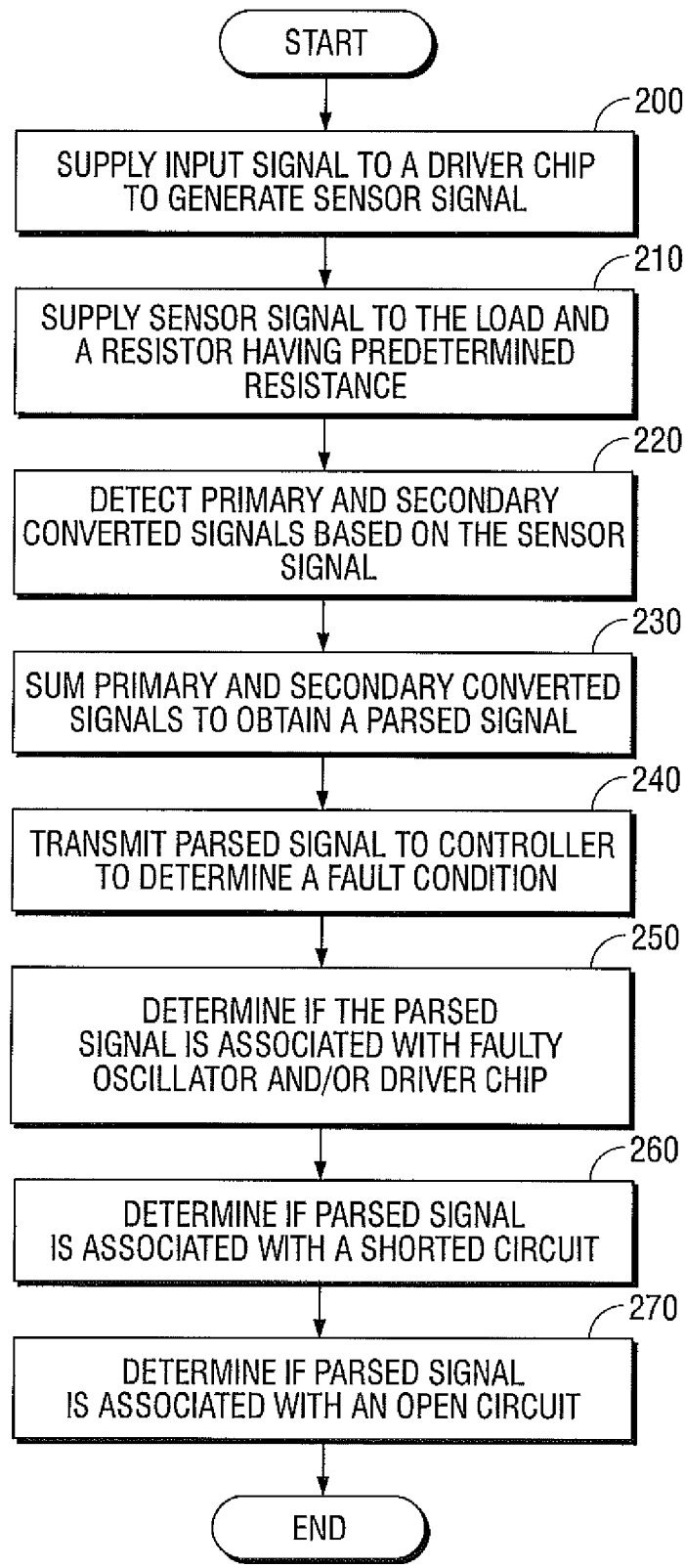
FIG. 6 is a flow chart illustrating a method according to another embodiment of the present disclosure.

FIG. 6 illustrates a method for determining a fault condition based on the $V_{out}$ signal supplied by the monitoring circuit 22b. In step 200, the oscillator 42 supplies an input signal to the driver 40, which generates a sensor signal. In step 210, the sensor signal is supplied to the resistor 46 having a predetermined resistance, $Z_{out}$ and to the load 48 through the isolation transformer. In step 220, primary and secondary converted signals are detected based on the sensor signal and the oscillator signal, respectively. In step 230, the primary and secondary converted signals are summed at the summer 58 to obtain a parsed signal. In step 240, the summer 58 transmits the parsed signal to the controller 24 which determines if there is a fault detected by or associated with the monitoring circuit 22b. In step 250, the controller 24 determines if the parsed signal is associated with a faulty oscillator 42 and/or the driver 40. In other words, if the $V_{out}$ is approximately 0. In step 260, the controller 24 determines if the parsed signal is associated with a shorted circuit, such as when the primary converted signal is approximately 0, since the secondary converted signal is equal to the DC offset and the parse signal is going to be equal to the DC offset. In step 270, the controller 24 determines whether $V_{out}$ is associated with $Z_{out}$ being much larger than $Z_{out}$—a condition reflective of an open circuit.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An impedance monitoring circuit for an electrosurgical generator, the monitoring circuit comprising:
    an isolation transformer coupled to at least one of an active terminal and a return terminal of an electrosurgical generator, wherein the isolation transformer includes a primary winding coupled to a reference resistor and a secondary winding coupled to a load;
    a driver configured to transmit a sensor signal to the reference resistor and the load;
    a primary converter coupled to the reference resistor and the load and configured to detect a primary converted signal as a function of the sensor signal passing through the reference resistor and the load;
    a secondary converter coupled to the driver and configured to detect a secondary converted signal as a function of the sensor signal prior to passing through the reference resistor and the load; and
    a controller including a preprogrammed offset value, wherein the controller is configured to determine a fault condition based on the primary and secondary converted signals and the offset value.

2. The impedance monitoring circuit according to claim 1, wherein the driver is a level shifter driver chip coupled to an oscillator configured to supply an oscillator signal thereto, and wherein the driver is configured to increase at least one of voltage and current of the oscillator signal.

3. The impedance monitoring circuit according to claim 2, wherein the controller is configured to determine existence of a fault condition with at least one of the driver and the oscillator when an amplitude of both of the primary and secondary converted signals is approximately 0 V.

4. The impedance monitoring circuit according to claim 2, wherein the controller is configured to determine existence of a short circuit condition when an amplitude of the primary converted signal is approximately 0 V.

5. The impedance monitoring circuit according to claim 1, wherein the reference resistor has a predetermined resistance from 1 kΩ to 10 kΩ.

6. The impedance monitoring circuit according to claim 5, wherein the controller is configured to determine existence of an open circuit condition when a resistance of the load is larger than the predetermined resistance of the reference resistor.

7. An impedance monitoring circuit for an electrosurgical generator, the monitoring circuit comprising:
    an isolation transformer coupled to at least one of an active terminal and a return terminal of an electrosurgical generator, wherein the isolation transformer includes a primary winding coupled to a reference resistor and a secondary winding coupled to a load;
    a driver configured to transmit a sensor signal to the reference resistor and the load;
    a primary converter coupled to the reference resistor and the load and configured to detect a primary converted signal as a function of the sensor signal passing through the reference resistor and the load;

a secondary converter coupled to the driver and configured to detect a secondary converted signal as a function of the sensor signal prior to passing through the reference resistor and the load; and a controller configured to determine a fault condition based on the primary and secondary converted signals.

8. The impedance monitoring circuit according to claim 7, wherein the driver is a level shifter driver chip coupled to an oscillator configured to supply an oscillator signal thereto, and wherein the driver is configured to increase at least one of voltage and current of the oscillator signal.

9. The impedance monitoring circuit according to claim 8, wherein the controller is configured to determine existence of a fault condition with at least one of the driver and the oscillator when an amplitude of both of the primary and secondary converted signals is approximately 0.

10. The impedance monitoring circuit according to claim 8, wherein the controller is configured to determine existence of a short circuit condition when an amplitude of the primary converted signal is approximately 0.

11. The impedance monitoring circuit according to claim 7, wherein the reference resistor has a predetermined resistance from 1 k$\Omega$ to 10 k$\Omega$.

12. The impedance monitoring circuit according to claim 11, wherein the controller is configured to determine existence of an open circuit condition when a resistance of the load is larger than the predetermined resistance of the reference resistor.

13. A method for detecting a fault in an impedance monitoring circuit, the method comprising the steps of:

transmitting a sensor signal to a reference resistor coupled to a primary winding of an isolation transformer and a load coupled to a secondary winding of the isolation transformer;

detecting a primary converted signal as a function of the sensor signal passing through the reference resistor and the load;

detecting a secondary converted signal as a function of the sensor signal prior to passing through the reference resistor and the load; and determining a fault condition based on the primary and secondary converted signals.

14. The method according to claim 13, wherein the transmitting step further includes the step of supplying an oscillator signal from an oscillator to a driver, wherein the driver is configured to increase at least one of voltage and current of the oscillator signal.

15. The method according to claim 14, wherein the determining step further includes the step of determining existence of a fault condition with at least one of the driver and the oscillator when an amplitude of both of the primary and secondary converted signals is approximately 0.

16. The method according to claim 14, wherein the determining step further includes the step of existence of a short circuit condition when an amplitude of the primary converted signal is approximately 0.

17. The method according to claim 13, wherein the reference resistor of the transmitting step has a predetermined resistance from 1 k$\Omega$ to 10 k$\Omega$.

18. The method according to claim 17, wherein the determining step further includes the step of determining existence of an open circuit condition when a resistance of the load is larger than the predetermined resistance of the reference resistor.

* * * * *